(12) United States Patent
Andrews et al.

(10) Patent No.: US 8,124,931 B2
(45) Date of Patent: Feb. 28, 2012

(54) METHOD AND APPARATUS FOR OIL SPILL DETECTION

(75) Inventors: Albert Ballard Andrews, Wilton, CT (US); Wei-Chuan Shih, Cambridge, MA (US); Matthew Clayton, Houston, TX (US); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 709 days.

(21) Appl. No.: 12/188,141

(22) Filed: Aug. 7, 2008

(65) Prior Publication Data

US 2009/0039255 A1    Feb. 12, 2009

Related U.S. Application Data

(60) Provisional application No. 60/955,216, filed on Aug. 10, 2007.

(51) Int. Cl.
  *G01T 1/169* (2006.01)
(52) U.S. Cl. ........................ 250/301; 250/461.1; 250/394
(58) Field of Classification Search .................. 250/301, 250/484.2, 339.14, 428, 432 R, 393, 394, 250/253, 461.1
See application file for complete search history.

(56) References Cited

U.S. PATENT DOCUMENTS

| | | | |
|---|---|---|---|
| 3,603,952 A * | 9/1971 | Smith | ...................... 340/539.26 |
| 4,933,678 A | 6/1990 | Tennyson | |
| 5,266,800 A | 11/1993 | Mullins | |
| 5,281,826 A | 1/1994 | Ivancic et al. | |
| 5,331,156 A | 7/1994 | Hines et al. | |
| 5,381,002 A | 1/1995 | Morrow et al. | |
| 5,443,712 A | 8/1995 | Dawans et al. | |
| 5,461,236 A | 10/1995 | Gram et al. | |
| 5,481,904 A | 1/1996 | Fleck, Sr. et al. | |
| 5,532,679 A | 7/1996 | Baxter, Jr. | |
| 5,742,053 A | 4/1998 | Rekunyk et al. | |
| 5,777,483 A | 7/1998 | Bailey | |
| 6,141,096 A * | 10/2000 | Stern et al. | ..................... 356/318 |
| 6,184,980 B1 * | 2/2001 | Brown et al. | ................. 356/300 |
| 6,665,074 B2 | 12/2003 | Huang et al. | |
| 6,822,742 B1 | 11/2004 | Kalayeh et al. | |
| 6,839,636 B1 | 1/2005 | Sunshine et al. | |
| 6,995,846 B2 | 2/2006 | Kalayeh et al. | |
| 7,009,550 B2 | 3/2006 | Moeller-Jensen et al. | |

(Continued)

FOREIGN PATENT DOCUMENTS

JP        6273255        9/1994

(Continued)

OTHER PUBLICATIONS

Lennon et al. "Detection and Mapping of Oil Slicks in the Sea by Combined Use of Hyperspectral Imagery and Laser-Induced Fluorescence," EARSeI EProceedings, vol. 5, No. 1; published Mar. 23, 2006; Retrieved from Internet [Apr. 8. 2011]; Retreived from URL <http://www.eproceedings.org/static/vol05_1/05_1_lennon1.pdf>.*

(Continued)

*Primary Examiner* — David Porta
*Assistant Examiner* — Yara Green

(57) ABSTRACT

The invention relates to a method for detecting the presence of hydrocarbons near an unmanned offshore oil platform. The method steps include monitoring reflected atmospheric and thermal radiation, detecting the presence of hydrocarbons, and generating an alert based on the presence of hydrocarbons.

23 Claims, 12 Drawing Sheets

U.S. PATENT DOCUMENTS

| 7,227,139 B2 | 6/2007 | Kram et al. |
| 2005/0134859 A1 | 6/2005 | Kalayeh et al. |
| 2006/0091310 A1 | 5/2006 | Furry |

FOREIGN PATENT DOCUMENTS

| JP | 2002-214140 | * | 7/2002 |
| WO | 2005064316 | | 7/2005 |

OTHER PUBLICATIONS

JP 2002-214140 Machine Translation.*

Skou, "Microwave Radiometry for Oil Pollution Monitoring, Measurements, and Systems," IEEE Transactions on Geoscience and Remote Sensing, vol. GE-24, No. 3, May 1986, pp. 360-367; Retrieved from internet [Oct. 12, 2011], Retrieved from URL <http:ieeexplore.ieee.org/iel5/36/40724600472472.pdf>/.*

Pelyushenko, "Microwave Radiometer Systems for the Detection of Oil Slicks," Spill Science & Technology Bulletin, vol. 2, No. 4, pp. 249-254, 1995; Retrieved from internet [Oct. 11, 2011], Retreived from url: <http://www.mendeley.com/research/microwave-radiometer-system-for-the-detection-of-oil-slicks>.*

Chang et al., "A region-based GLRT detection of oil spills in SAR images," Pattern Recognition Letters 29, (2008), pp. 1915-1923; Retrieved from intenet [Oct. 12, 2011], Retrieved from url: <http://linkingub.elsevier.com/retrieve/pii/S016786550800192X.*

Hus, L., Remote Sensing of Oil Spills in Thermal Infrared—Contour Line Effect, Geoscience and Remote Sensing Symposium 1991, IGARSS '91, Jun. 1991, 3 pages.

Horvath, R., Morgan, W. L, and Stewart, S. R., Optical Remote Sensing of Oil Slicks: Signature Analysis and Systems Evaluation, Oct. 1971, 23 pages.

Fingas, M. F. and Brown, C. E., Review of Oil Spill Remote Sensing, Presented as Spillcon 2000, Darwin, Australia, Aug. 16, 2000, 19 pages.

* cited by examiner

COUNT: 21280       MIN: 68
MEAN: 97.254       MAX: 123
STD DEV: 9.743     MODE: 103 (1015)

COUNT: 21280      MIN: 74
MEAN: 93.639      MAX: 111
STD DEV: 3.936    MODE: 94 (2301)

COUNT: 21280      MIN: 62
MEAN: 102.619     MAX: 173
STD DEV: 31.803   MODE: 84 (1034)

METHOD AND APPARATUS FOR OIL SPILL DETECTION

CROSS REFERENCE TO RELATED APPLICATIONS

This application claims priority under 35 U.S.C. §119(e) from Provisional Patent Application No. 60/955,216 filed Aug. 10, 2007, which is hereby incorporated by reference. Subject matter contained herein may be related to patent application Ser. No. 11/648,089 filed Dec. 29, 2006.

BACKGROUND

Oil spill detection methods can be broadly classified into global or local. Global detection schemes are typically satellite based (e.g., Landsat program managed by NASA and U.S. Geological Survey). Satellite systems perform large scale surveys; their primary limitations are low spatial resolution, low sampling rate and dependency on cloud cover. Local detection methods comprise of many different schemes including airborne (e.g., Light Detection and Ranging (LIDAR)) and shipboard (e.g., microwave radar) monitoring systems. Shipboard and airborne systems are capable of providing higher resolution than satellite based systems, but are not ideal for permanent monitoring applications. Therefore, such systems are designed as mobile units.

The current system for monitoring oil seeps from unmanned offshore platforms in the Gulf of Mexico includes daytime, fair-weather helicopter sorties. It is desirable to reduce the number of helicopter sorties, providing a fixed monitoring system that transmits the sensor data streams (e.g., image stream, video stream, etc.) via a wireless network to a manned platform where the data is processed. It is further desirable that an automated alert is generated when an oil spill occurs and the operator is notified such that upon further investigation if the alert is deemed to be genuine, a helicopter may be dispatched to the platform for a thorough on-site investigation. It is further desirable for the system to run 24/7 in all weather conditions to improve over current methodology, both in regularity and safety.

Thermal imaging was originally developed for military applications. The first practical barium strontium titanate (BST) ferroelectric infrared detectors (by Raytheon) and vanadium oxide (VOx) microbolometers (by Honeywell) became available for non-military commercial applications only recently in the 1990s. Thermal imaging is utilized in many industrial applications, as well as security, firefighting, and law enforcement. An advantage of thermal imaging is its nighttime capability without artificial illumination.

Previously mentioned mobile units have high power consumption and unreliable network connectivity. This aspect is addressed more fully in a related patent application Ser. No. 11/648,089 filed Dec. 29, 2006, which is hereby incorporated by reference. Related patent application Ser. No. 11/648,089 entitled "Method and Apparatus for Evaluating Data Associated with an Offshore Energy Platform", in one or more embodiments, describes a system for transmitting data from an unmanned offshore energy platform to a manned offshore energy platform via a wireless network powered by solar panels, wind turbines, and other alternative energy generation schemes.

SUMMARY

In general, in one aspect, the invention relates to a method for detecting the presence of hydrocarbons near an unmanned offshore oil platform. The method steps include monitoring reflected atmospheric and thermal radiation, detecting the presence of hydrocarbons, and generating an alert based on the presence of hydrocarbons.

In general, in one aspect, the invention relates to a method for detecting presence of hydrocarbons on a surface. The method steps include monitoring surface emission from the surface in an infrared band, providing a model for modeling emissivity contrast of the surface emission, wherein the emissivity contrast is induced by the presence of hydrocarbons on the surface, detecting the presence of hydrocarbons from the surface emission based on the model, and generating an alert based on the presence of hydrocarbons.

In general, in one aspect, the invention relates to a system for detecting presence of hydrocarbons on a surface. The system includes a plurality of sensors for monitoring reflected atmospheric radiation and surface emission from the surface, and a memory and a processor, embodying instructions stored in the memory and executable by the processor, the instructions comprising functionality to detect the presence of hydrocarbons based on the reflected atmospheric radiation and the surface emission according to a decision tree, where the decision tree is based on a model for modeling radiance contrast of the reflected atmospheric radiation and the surface emission in at least one selected from a group consisting of daytime condition, nighttime condition, and pre-determined weather condition, wherein the radiance contrast is induced by the presence of hydrocarbons on the surface and comprises at least one selected from a group consisting of reflection contrast, temperature contrast, and emissivity contrast, and generate an alert based on the presence of hydrocarbons.

In general, in one aspect, the invention relates to a system for detecting presence of hydrocarbons on a surface. The system includes a plurality of sensors for monitoring surface emission from the surface in an infrared band, and a memory and a processor, embodying instructions stored in the memory and executable by the processor, the instructions comprising functionality to detect the presence of hydrocarbons based on the surface emission using a model for modeling emissivity contrast of the surface emission, wherein the emissivity contrast is induced by the presence of hydrocarbons on the surface and comprises at least one selected from a group consisting of temperature contrast, spectral contrast and thickness contrast, and generate an alert based on the presence of hydrocarbons.

Other aspects and advantages of the invention will be apparent from the following description and the appended claims.

BRIEF DESCRIPTION OF THE DRAWINGS

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
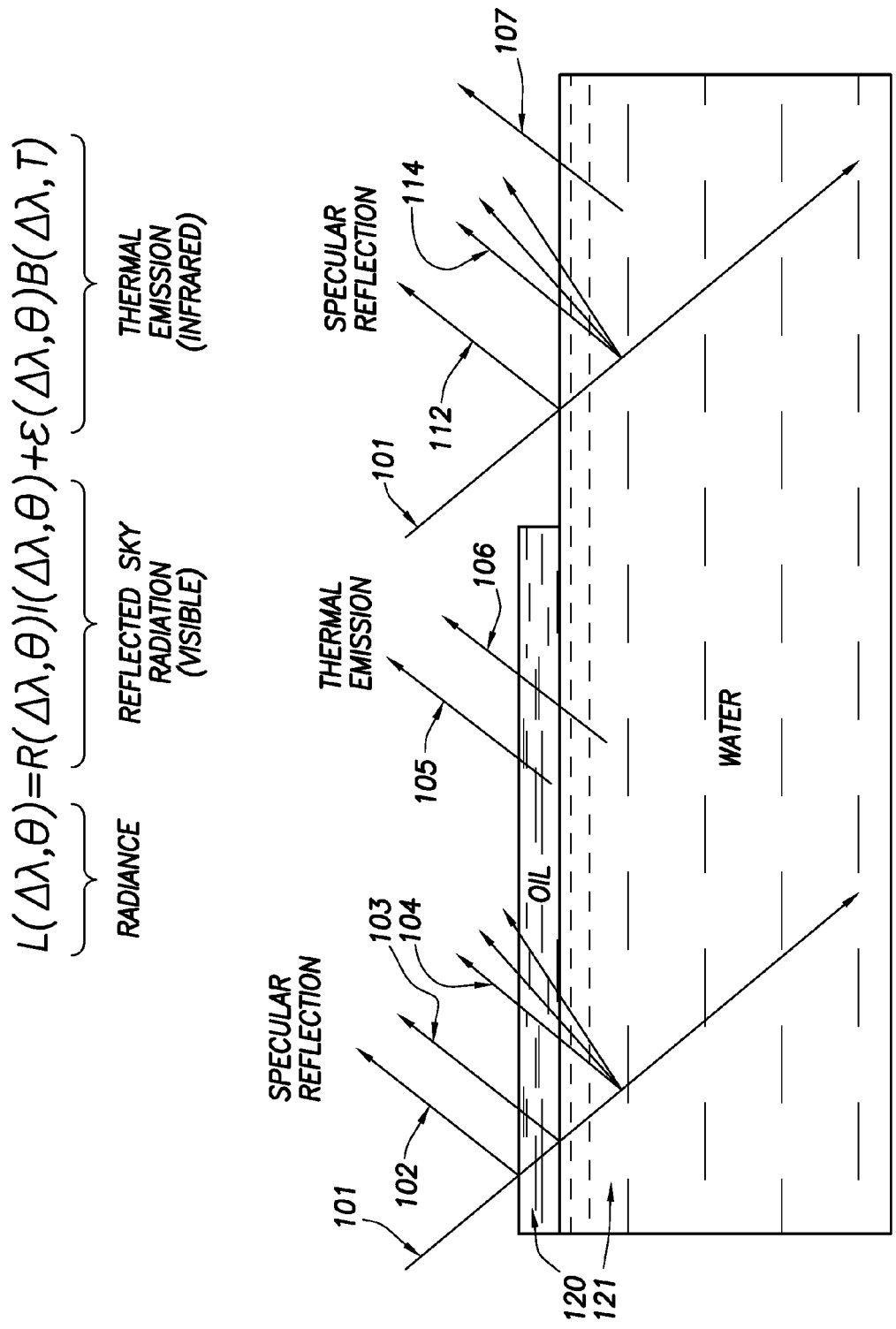
FIG. 1 shows an exemplary cross sectional view of oil on water surface in accordance with one or more embodiments of the invention.

Specific embodiments of the invention will now be described in detail with reference to the accompanying Figures. Like elements in the various Figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a system and method for detecting presence of hydrocarbon on a surface. In one or more embodiments of the invention, oil spills from unmanned offshore platforms are permanently monitored using a combination of sensors (e.g., thermal, electromagnetic, chemical, etc.) to detect hydrocarbon films that appear on the surface of the water in the vicinity of platform.

The present invention provides monitoring capability during an entire 24 hour/7 days a week period. In one embodiment, the video streams from two cameras (e.g., for visible and long-wave-infrared (LWIR) bands) are transmitted via a wireless network to a manned platform as described in the related patent application Ser. No. 11/648,089, entitled "Method and Apparatus for Evaluating Data Associated with an Offshore Energy Platform" and filed Dec. 29, 2006, and incorporated by reference above. The data streams are then analyzed by the acquisition software on the host computer located on the manned platform.

In one embodiment, a LWIR (with nominally 7-14 μm wavelength, also known as far-infrared (far-IR or FIR)) thermal imager (sensor) provides a video stream, which is monitored by an operator at a remote location. A series of image processing operations are performed on individual frames from the video stream and an automated alert is triggered when a spill occurs to notify the operator. Additionally, data streams from a variety of other sensors, including but not limited to a visible camera with night vision capability, RF sensors, chemical sensors, Raman sensors, and fluorescence sensors, may be configured to provide additional cross checks on the alerts generated by the LWIR camera.

FIG. 1 shows an exemplary cross sectional view of an oil spill on a water surface in accordance with one or more embodiments of the invention. As shown in FIG. 1, an oil film (120) floats atop a body of water (121) with incident atmospheric (e.g., sky) radiation (101) being reflected off the oil covered surface (denoted as "oil/water" or "o/w" unless otherwise specified in equations below) and the native water surface (denoted as "water" or "w" unless otherwise specified in equations below). Image contrast between the oil covered surface and the native water surface may exist if there is a difference in the surface radiance of the two surfaces in a certain wavelength band. The surface radiance depends mostly on reflected atmospheric radiation (e.g., (102), (103), (104), (112), and (114)) and surface emission (or thermal emission, e.g., (105), (106), and (107)). Generally speaking, the reflected atmospheric radiation term dominates for measurements taken in the visible wavelength band, whereas the surface emission dominates in the IR band.

Image contrast $C(\Delta\lambda, \theta)$ occurs when there is a difference in the surface radiance $L(\Delta\lambda, \theta)$ between the oil covered surface and the native water surface as shown in Equation 1 below.

$$C(\Delta\lambda,\theta)=Tr(d,\Delta\lambda)[L_{Oil}(\Delta\lambda,\theta)-L_{water}(\Delta\lambda,\theta)] \quad \text{Equation 1}$$

$\Delta\lambda$ is the wavelength band. $\theta$ is the detection angle. $Tr(d, \Delta\lambda)$ is the transmission through the atmosphere. $L_{Oil}(\Delta\lambda, \theta)$ and $L_{Water}(\Delta\lambda, \theta)$ are the surface radiance for the oil covered surface and the native water surface, respectively.

The surface radiance depends on reflected atmospheric radiation and surface emission as shown in Equation below.

$$L(\Delta\lambda,\theta)=R(\Delta\lambda,\theta)I(\Delta\lambda,\theta)+\epsilon(\Delta\lambda,\theta)B(\Delta\lambda,T) \quad \text{Equation 2}$$

T is the temperature. $L(\Delta\lambda, \theta)$ is the surface radiance for the oil covered surface or the native water surface. $R(\Delta\lambda, \theta)$ is the reflectivity of the surface. $I(\Delta\lambda, \theta)$ is the intensity of the incident radiation (e.g., of the atmosphere). $\epsilon(\Delta\lambda, \theta)$ is the emissivity of the surface. $B(\Delta\lambda, t)$ is the thermal emission due to the Planck function as shown in Equation 3 below.

$$B(\Delta\lambda,T)=C_1\lambda^{-5}[\exp(C_2/\lambda T)-1]^{-1} \quad \text{Equation 3}$$

The Planck function, also referred to as the black body radiation function, represents the maximum amount of radiation that a material can emit at a given temperature and wavelength. The emissivity $\epsilon(\Delta\lambda, \theta)$ is defined as the ratio of emitted radiation to black body radiation.

Radiometric temperature is defined as the temperature T at which a black-body described by Equation 3 would yield an equivalent amount of emission over a band $\Delta\lambda$ as the actual emission from a material measured by a sensor with an effective bandpass $\Delta\lambda$. Both higher physical temperature and higher emissivity of the material contribute to higher surface radiance therefore higher radiometric temperature. That is, a difference in the emissivity of two materials in thermal equilibrium results in an apparent radiometric temperature difference.

When an oil film (e.g., (120)) appears on a body of water (e.g., (121)) due to spillage, the emissivity difference between oil and water results in a radiometric temperature difference even if the oil film is in thermal equilibrium with the water. In certain conditions, the radiometric temperature difference may be approximately 1K in the IR range of the electromagnetic spectrum. In one or more embodiments of the invention, a thermal imaging camera with sensitivity better than 0.1K is able to detect image contrast between the oil covered surface and the native water surface at nighttime even without the contribution from reflected atmospheric radiation. In one or more embodiments of the invention, the detection region of IR imaging cameras utilizing either BST or VOx type sensors (nominally 8-14 microns) covers terrestrial radiation whose Planck distribution peaking at nominally 10 microns. Accordingly, the un-cooled detector having a thermal sensitivity of better than about 0.1K may be used to detect image contrast of the oil covered surface and the native water surface in the LWIR bands.

Because oil is a better absorber than water in the 8-14 micron wavelength band, differential heating from atmospheric radiation (e.g., solar radiation) causes the temperature of the oil film to rise higher relative to the surrounding water during daytime. In one or more embodiments of the invention, differential heating from incident atmospheric radiation of oil relative to water further increases the image contrast at daytime. In one or more embodiments of the invention, surface radiance contrasts from fluorescence and Raman scattering may also be induced by irradiating water surface from a source of electromagnetic radiation. This external radiation may be continuous or at discrete times to induce continuous or time gated radiance detection accordingly.

Generally speaking, image classification pertains to the adoption of decision rules for sorting pixels into classes. For example, images may be automatically categorized into classes (or themes) based on all pixels in each image. These may be performed based on either parametric methods using statistical parameters (e.g., mean and standard deviation of pixel distribution) or non-parametric methods to detect objects (e.g., polygons) in the feature space. These methods have been adopted in the remote sensing community, for example for classification of Landsat images into water, vegetation types, terrain types, etc. In one or more embodiments of the invention, image classification based on parametric method and/or non-parametric method may be applied using multiple spectral bands (or wavelength bands, e.g., visible, NIR, LWIR, etc.) for oil spill detection, as described below.

Figure 2:
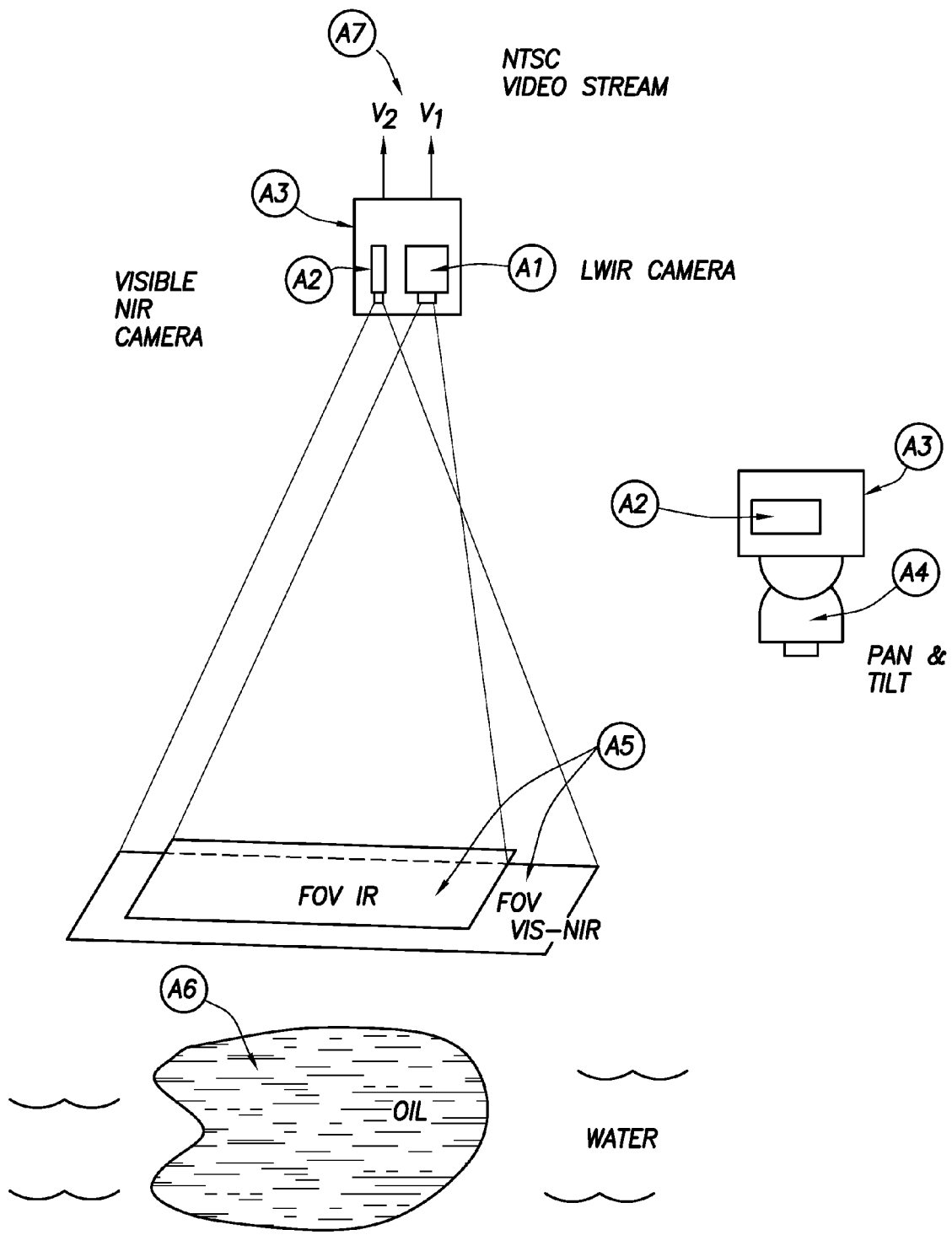
FIG. 2 shows an exemplary graphical depiction of an oil detection system in accordance with one or more embodiments of the invention.

In accordance with the present invention, FIG. 2 shows a possible embodiment for an oil detection system. Those skilled in the art, having the benefit of this detailed description, will appreciate the components shown in FIG. 2 may differ among embodiments of the invention, and that one or more of the components may be optional. In one or more embodiments of the invention, one or more of the components shown in FIG. 2 may be omitted, repeated, supplemented, and/or otherwise modified from that shown in FIG. 2. Accordingly, the specific arrangement of components shown in FIG. 2 should not be construed as limiting the scope of the invention.

As shown in FIG. 2, the LWIR sensor (A1) and visible/NIR night vision video camera (A2) are mounted in a weather-proof housing (A3). The housing is attached to a positioning device (A4) with pan and tilt capability. The visible and LWIR cameras have overlapping field of views (FOV LWIR and FOV VIS-NIR) (A5). An oil spill (A6) may be completely encompassed by the FOV, or partly occluded. In the latter case the pan and tilt mechanism is periodically scanned over its full range of motion to obtain full coverage in a monitored area (e.g., the vicinity of the oil platform). Frame grabs (i.e., captured frames) from either of the two video streams (A7) may be captured at the same instant and overlaid using the data acquisition software.

Figure 3A:
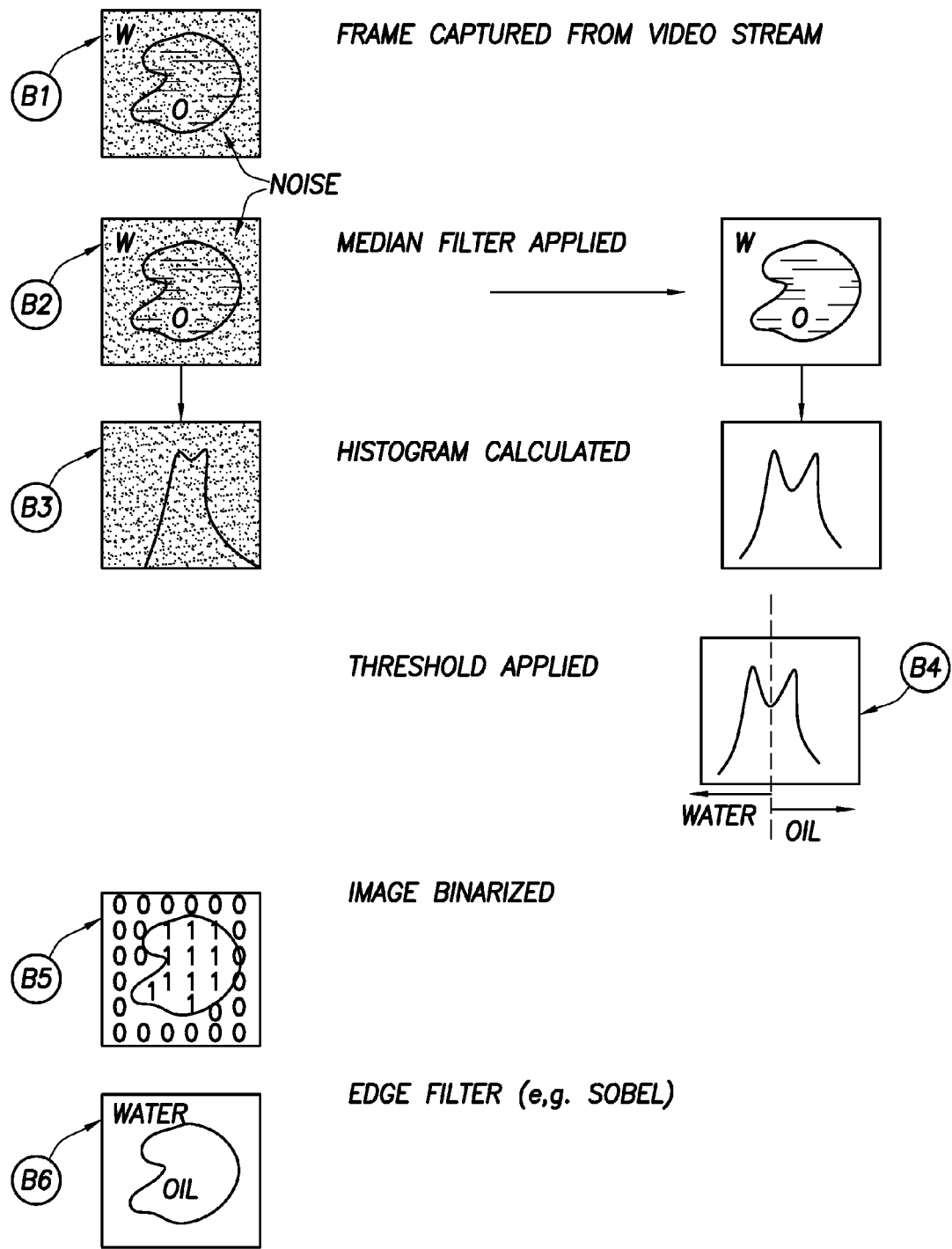
FIGS. 3A-3B show an exemplary graphical depiction of an oil detection workflow in accordance with one or more embodiments of the invention.
Figure 3B:
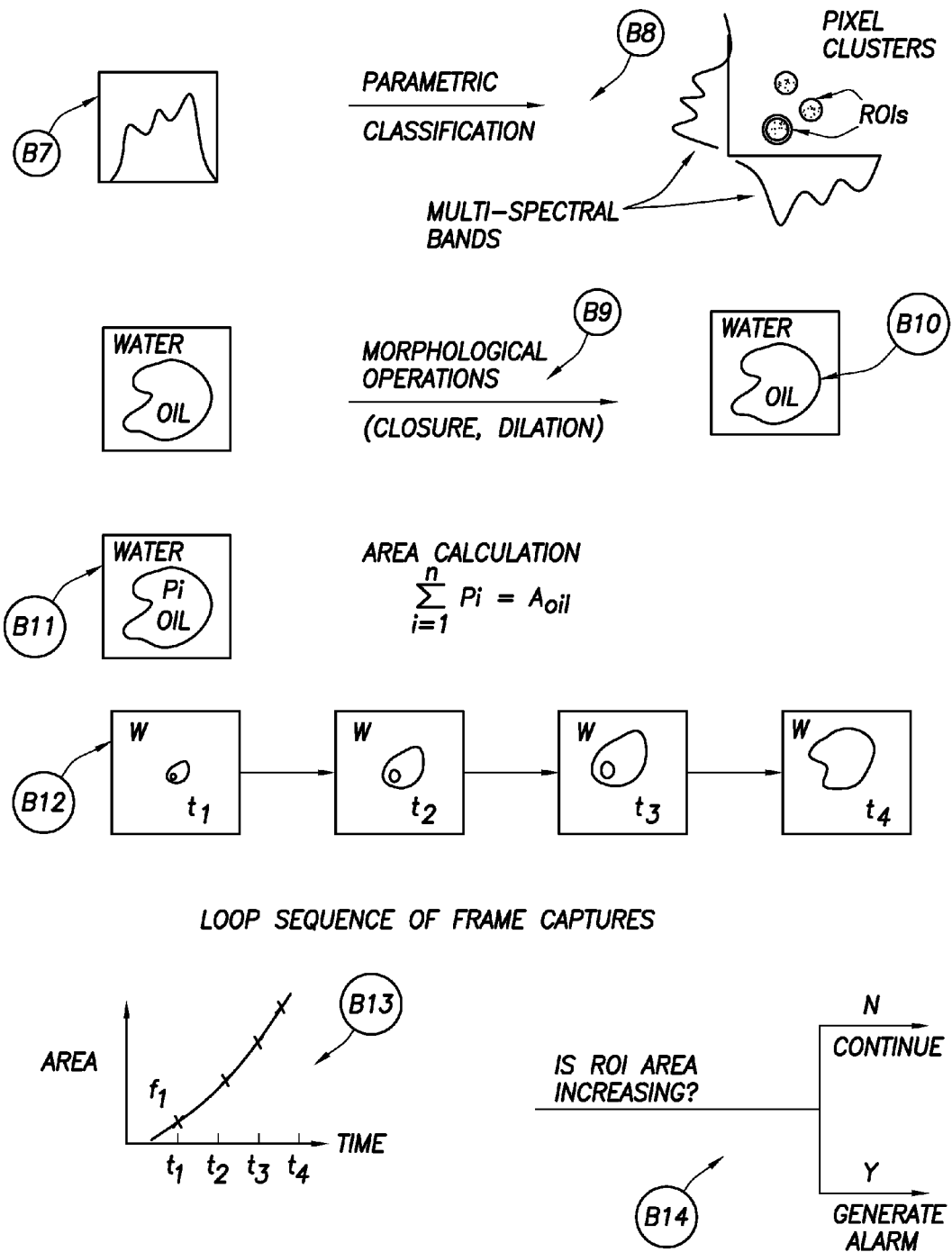
Figure 4A:
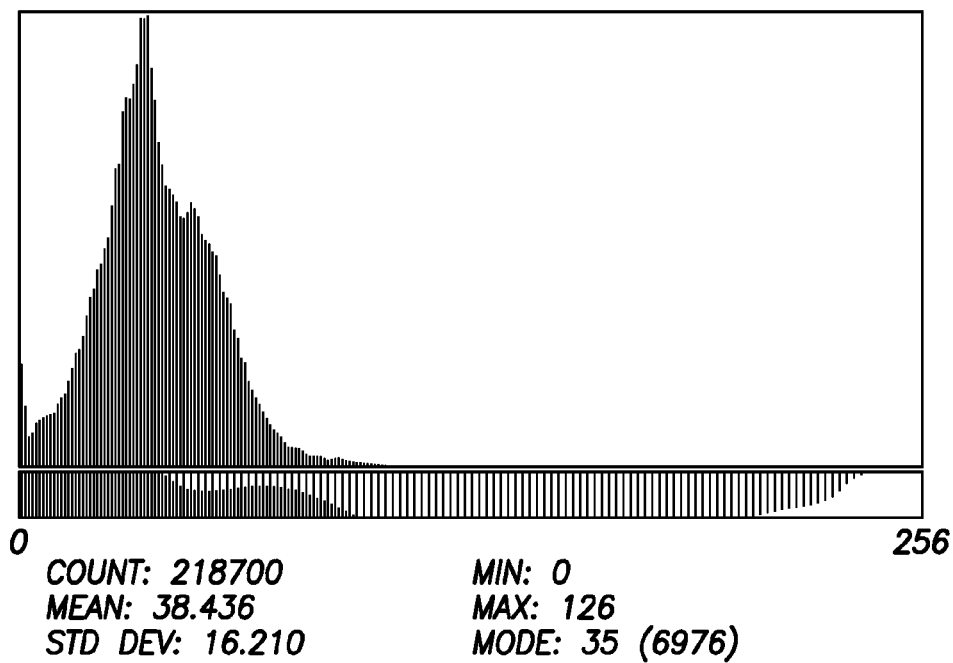
FIGS. 4A-6D show exemplary statistical diagrams in the oil detection workflow of FIGS. 3A-3B in accordance with one or more embodiments of the invention.
Figure 4B:
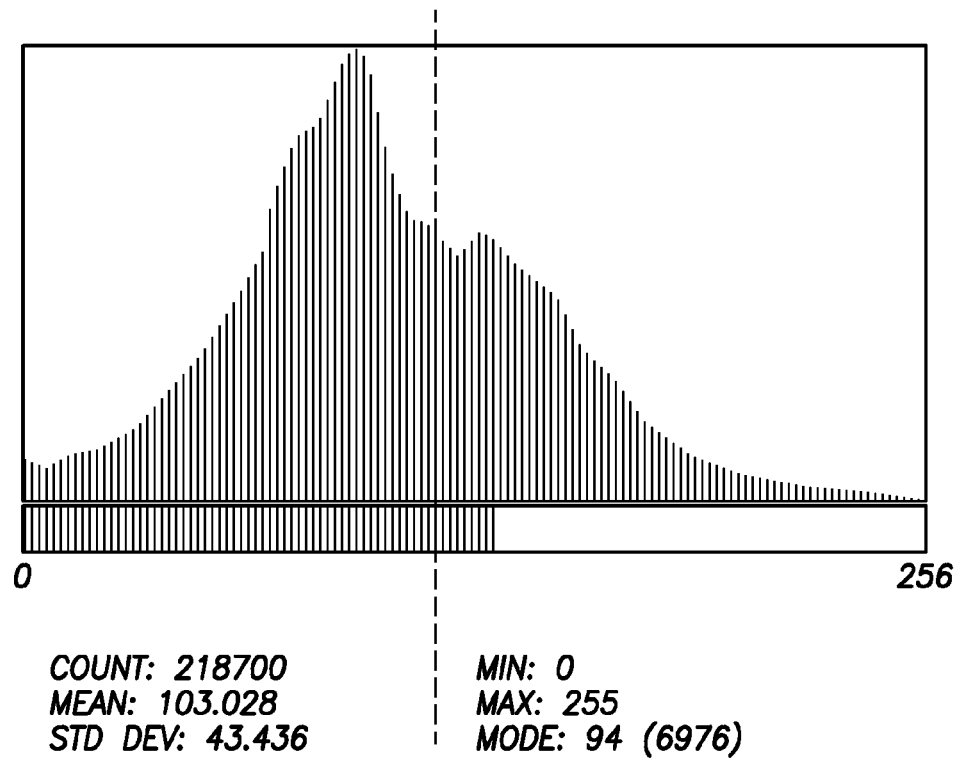
Figure 4C:

In one or more embodiments of the invention, frame grabs are periodically initiated by the data acquisition system, regardless of whether an operator is present to monitor the video stream. In accordance with the present invention, FIGS. 3A-3B depict one suitable sequence of operations performed on each sample frame grab (B1). First, as shown in FIG. 3A, a median filter (B2) is applied to de-speckle the image and remove random noise to generate a cleaned image. Next, the histogram (B3) of the frame grab (B1) is evaluated. If the cleaned image contains two or more resolved peaks (B4) (e.g., shown as the exemplary histogram in FIG. 4B), a threshold operation, (B5) is performed on the image pixel data to binarize the image. An exemplary binarized image is shown in FIG. 4C. Alternatively, an edge filter (B6) may be applied to the frame grab (B1).

In one or more embodiments of the invention, the histogram (B8) may be multi-dimensional based on pixel data obtained from multiple spectral bands (e.g., NIR, FIR, visible, etc.). Exemplary histograms with one to four resolved peaks are shown in detail in FIGS. 6A-6D, respectively where pixel intensity is represented by the axes labeled "BAND i" and pixel count is represented by density of the dots in the histogram.

As shown in FIG. 3B, if there are more than two peaks in the histogram (e.g., the exemplary histogram of FIGS. 6C and 6D), a parametric (statistical) image classification algorithm (B7) may be applied to identify region of interest (ROI) (e.g., the distinct clusters of dots in FIG. 6A-6D) in the histogram where pixel clusters and corresponding classes may be defined based on pre-determined decision rules. Once the pixels outside the region of interest (ROI) have been removed, a target surface object may be defined based on the remaining pixel clusters, which correspond to radiation originated from substantially oil and/or substantially water. The edge filtering operation (B6 in FIG. 3A) is followed by a series of morphological operations (B9), which result in boundary closing of the identified oil contaminated area (B10). The area of the oil spill (or other statistical parameter indicating a possible extent of oil spill) is then calculated by counting pixels (B11). These actions complete one cycle on a single frame grab (B1) from the video stream (A7 in FIG. 2). The procedure then loops back and starts over again for the next captured frame (B12). After each successive iteration cycle, a plot of the area versus time for the target surface object may be updated (B13). If the region is growing then an alert is generated (B14). When additional sensors are present, such as Raman sensor or Fluorescence sensor, the alert is first cross checked with inputs from these other sensor data streams prior to generating the alert. This may aid in the reduction of false positives.

In one or more embodiments of the invention, the image processing operations described above may be performed in the background if an operator is available to actively monitor the video streams (A7) form both cameras, as shown in FIG. 2. While viewing the live video, the operator may chose to trigger an alert based on personal expertise recognizing the characteristic features of an oil spill that occur in the different spectral bands (e.g., visible, NIR, LWIR, etc.). For example, during daylight hours, the visible camera (A2) provides continuous video coverage of the area underneath and adjacent to the oil platform. In essence, this video data stream is essentially equivalent to the visuals obtained by a pilot conducting helicopter sorties.

Figure 7A:
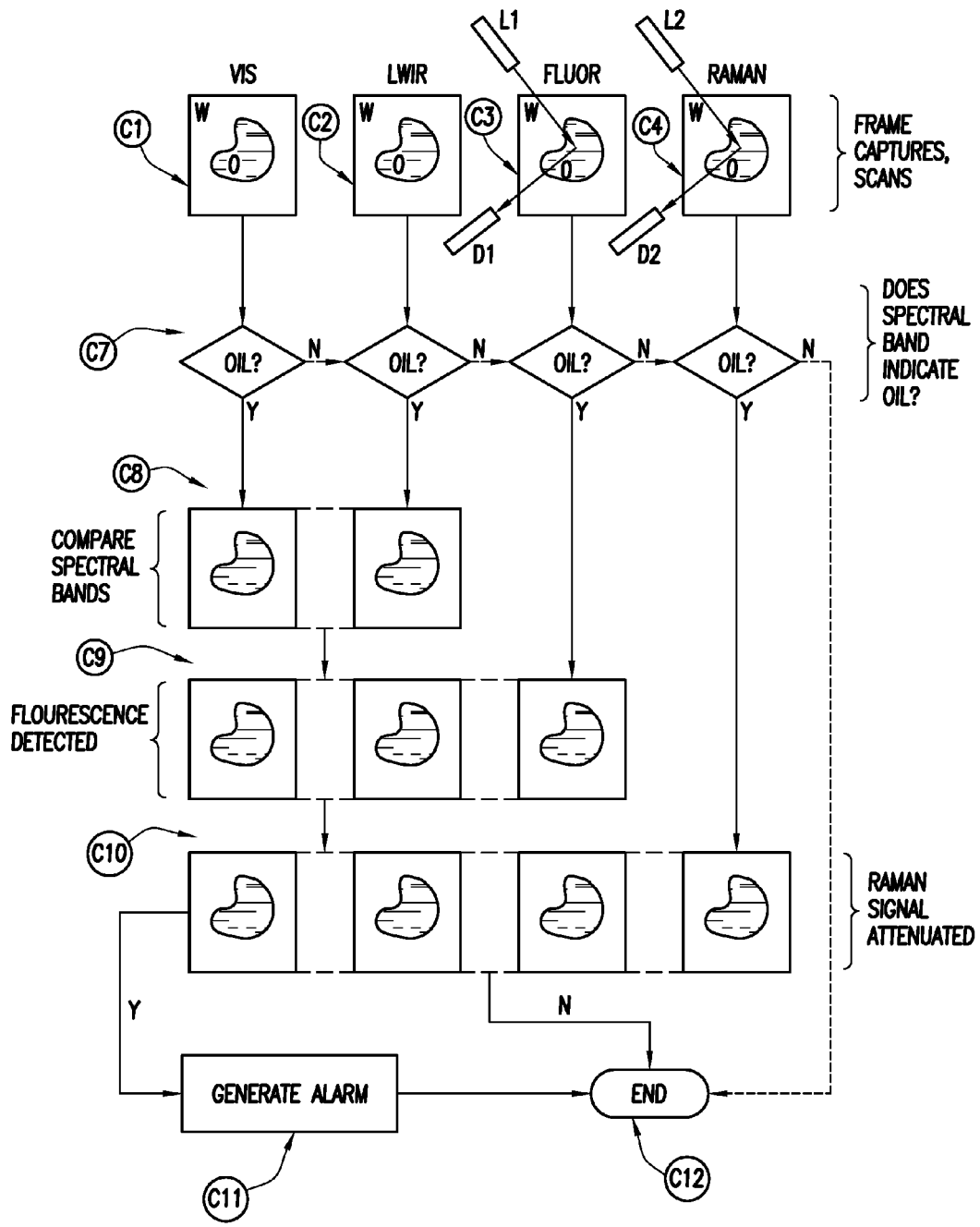
FIG. 7A shows an exemplary schematic diagram of a decision tree for oil detection in accordance with one or more embodiments of the invention.

FIG. 7A depicts an embodiment showing integration of image streams from multiple sensors in an exemplary decision tree for oil detection. The exemplary decision tree depicted in FIG. 7A includes responses from multiple sensors C1-C4, decision boxes C7, comparison boxes C8-C10, and action boxes C11-C12. As shown in FIG. 7A, a workflow following the decision tree results in reduced number of false detection generated by automated alarm system (e.g., as shown in FIG. 2) based on cross validation comparing image streams in different spectral bands from the multiple sensors. As shown in FIG. 7A, C1 is a visible (VIS) camera producing a video stream. C1 may also be configured to sense the near infrared (NIR) wavelength band (nominally 0.65-1.0 micron). C2 is a LWIR camera. C3 is a fluorescence detection system comprising an excitation light source L1 (e.g., a ultraviolet (UV) light source) and a detector D1. C4 is a Raman detection system including an excitation source L2 and a detector D2.

In accordance with one embodiment, data stream (e.g., image stream, video stream, etc.) from each sensor is monitored for hydrocarbon presence in a series of decision boxes C7. Each sensor response may be compared with any other sensor response. For example, the VIS and LWIR image streams are compared in comparison box C8 as both cameras may detect contrast between oil covered water surface and native water surface during daylight. In another example, the VIS, LWIR, and Fluorescence image streams are compared in comparison box C9. If image streams from C1 and/or C2 indicate hydrocarbon presence, then the monitored area in question may be irradiated with a UV light source L1 for the response recorded by D1 to be considered in conjunction with the responses from C1 and/or C2 in the comparison box C9. In yet another example, if the Raman signal obtained by C4 from water is attenuated indicating the possible presence of hydrocarbons, image streams from sensors C1, C2, and C3 are cross validated with the Raman signal from C4 in the comparison box C10.

Generally speaking, different sensors perform differently under various environmental conditions (e.g., daytime condition, nighttime condition, various weather conditions, etc.). In one or more embodiments of the invention, measured radiance contrast from each sensor channel (i.e., each camera and associated processing resource as depicted in FIG. 2 and FIGS. 3A-3B) may be modeled for each of these environmental conditions based on the theoretical radiance contrast as described by equations 1-3 above. In one or more embodiments of the invention, the radiance contrast model may include capabilities for modeling reflection contrast, temperature contrast, emissivity contrast, or suitable contrast based on other physical mechanisms. The reliability and/or confidence level of each sensor channel with respect to sensor sensitivity, background interference, image quality, and/or other relevant parameters may be established for various environmental conditions from this radiance contrast model.

In one or more embodiments of the invention, the decision tree depicted in FIG. 7A may be configured (or otherwise defined) based on the radiance model. For example, individual sensor channels best suited for each environment condition may be identified and the decision tree configured accordingly such that a positively detected oil spill response from a best suited sensor channel is capable to generate an alarm (C11) under the corresponding environmental condition independent of other sensor channels. Alternatively, each sensor channel may be assigned different weights in different environmental conditions, for example depending on the time of day and weather conditions. In one or more embodiments of the invention, the structure of the series of decision boxes C7 and/or the comparison boxes C8-C10 may be configured (or otherwise defined) based on the radiance model.

The automated alert system described above is advantageous for a number of reasons. As a first matter, helicopter flights are both expensive and dangerous. Secondly, a remote 24/7 monitoring system allows for improved detection frequency and reliability. The combination of a number of different sensor image streams reduces the number of false detections to an acceptable level. As a result, a helicopter needs to be dispatched to the platform following careful review of the alert history by an operator.

Figure 7B:
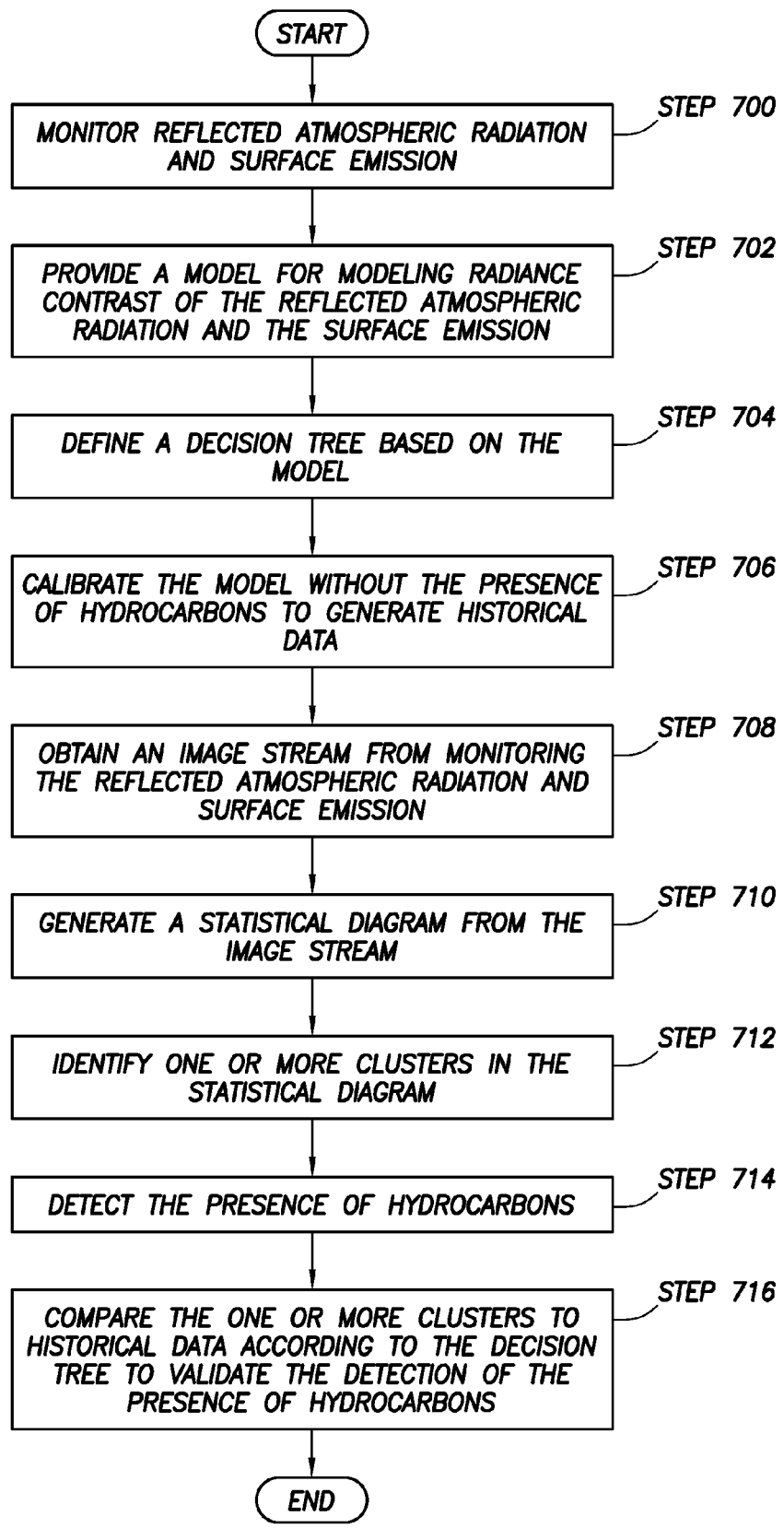
FIG. 7B shows a flow chart of a method based on the decision tree of FIG. 7A in accordance with one or more embodiments of the invention.

FIG. 7B is a flow chart of a method based on the decision tree of FIG. 7A in accordance with one or more embodiments of the invention. The process shown in FIG. 7B may be used, for example, by the oil detection system of FIG. 2. Those skilled in the art, having the benefit of this detailed description, will appreciate the sequence of steps shown in FIG. 7B may differ among embodiments of the invention, and that one or more of the steps may be optional. In one or more embodiments of the invention, one or more of the steps shown in FIG. 7B may be omitted, repeated, and/or performed in a different order than that shown in FIG. 7B. Accordingly, the specific arrangement of steps shown in FIG. 7B should not be construed as limiting the scope of the invention.

Initially, reflected atmospheric radiation (e.g., from solar illumination, atmospheric scattering, etc.) and surface emission (e.g., thermal emission) are monitored from the surface (e.g., water surface) (Step 700). In one or more embodiments, the monitoring may be performed using multiple sensor channels (e.g., a visible camera, a NIR camera, a FIR or LWIR camera, etc.), as described with respect to FIG. 2 above.

As described with respect to Equations 1-3 above, radiance contrast may be induced by the presence of hydrocarbons on the surface and may include reflection contrast, temperature contrast, emissivity contrast, or contrast based on other physical mechanisms. In Step 702, a model is provided for modeling the radiance contrast of the reflected atmospheric radiation and the surface emission. In one or more embodiments of the invention, the model is provided for modeling radiance contrast in daytime condition, nighttime condition, and/or other pre-determined weather conditions. In one or more embodiments of the invention, the model models measured radiance contrast obtained using an automated system of FIG. 2 configured to perform processing steps of FIGS. 3A-3B. In one or more embodiments of the invention, the model may be capable of estimating or otherwise establishing reliability and/or confidence level of each sensor channel in the automated system of FIG. 2 with respect to sensor sensitivity, background interference, image quality, and/or other relevant parameters for various environmental conditions.

In Step 704, a decision tree is defined based on the radiance contrast model to guide a workflow for detecting the presence of hydrocarbons (e.g., oil spill on the water surface). In one or more embodiments of the invention, the decision tree includes multiple sensor channels, decision boxes, comparison boxes, and alarm generation module, such as the decision tree depicted in FIG. 7A above.

In Step 706, the model is calibrated without the presence of hydrocarbons in a calibration phase to generate historical data, which may be used as references in the decision tree in a subsequent monitoring phase. For example, an image stream from any of the sensors C1-C4 during monitoring phase may be compared to the historical data in a corresponding decision box of C7.

Figure 5A:
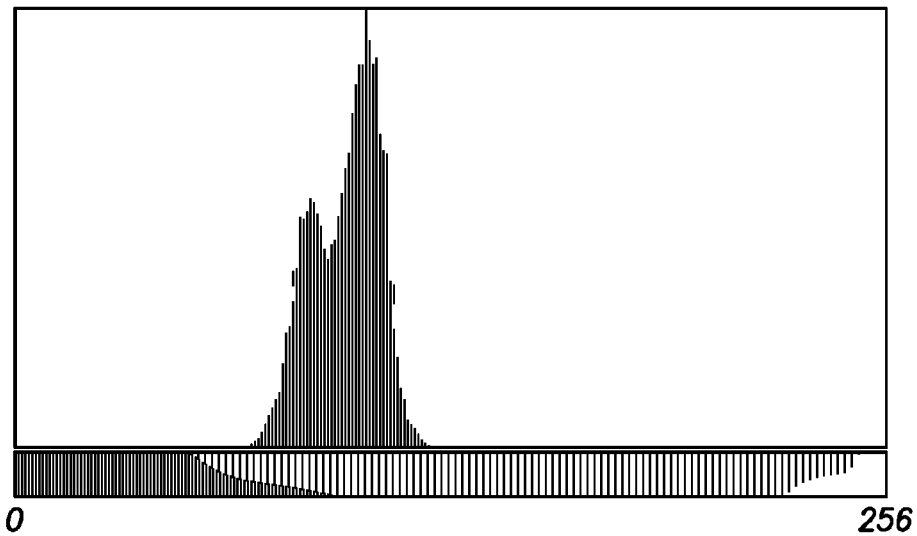
Figure 5B:
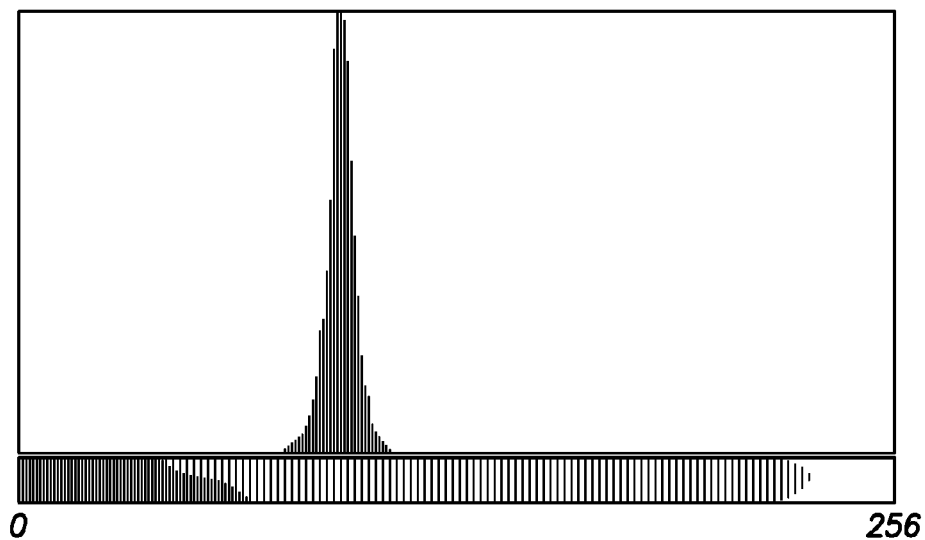
Figure 5C:
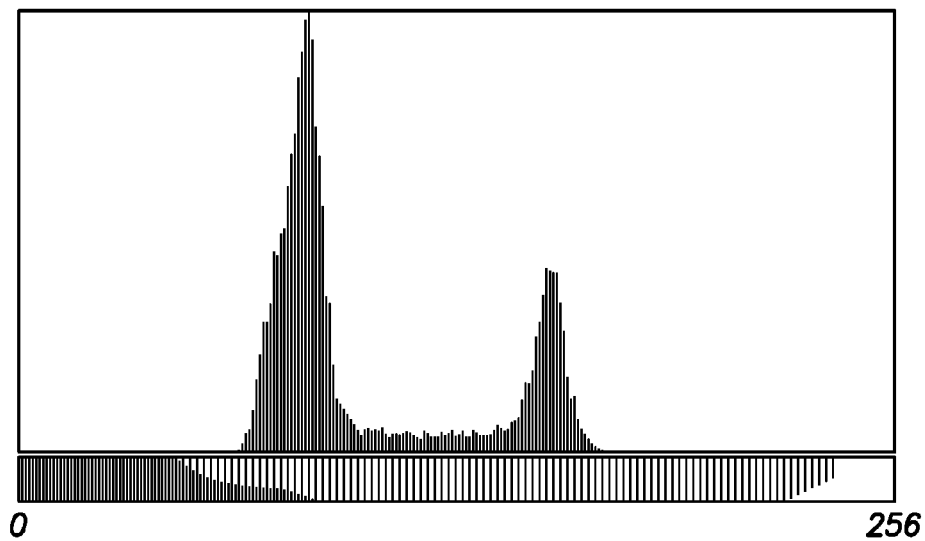
Figure 6A:
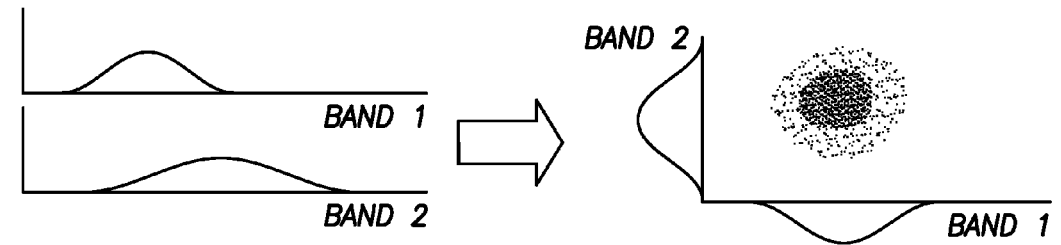
Figure 6B:
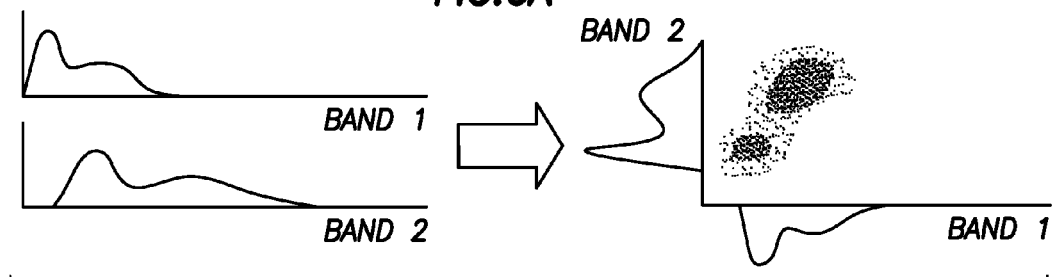
Figure 6C:
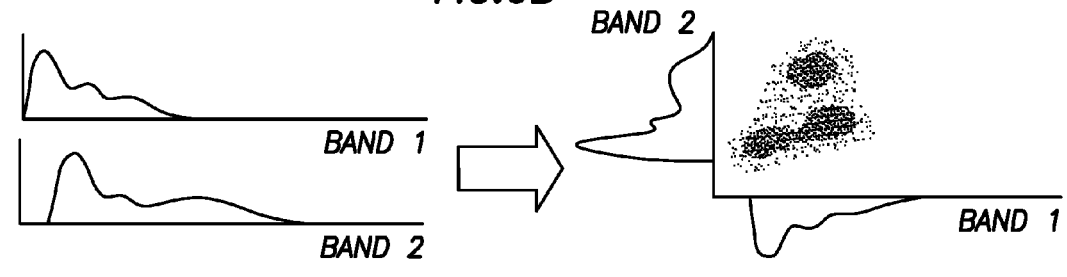
Figure 6D:
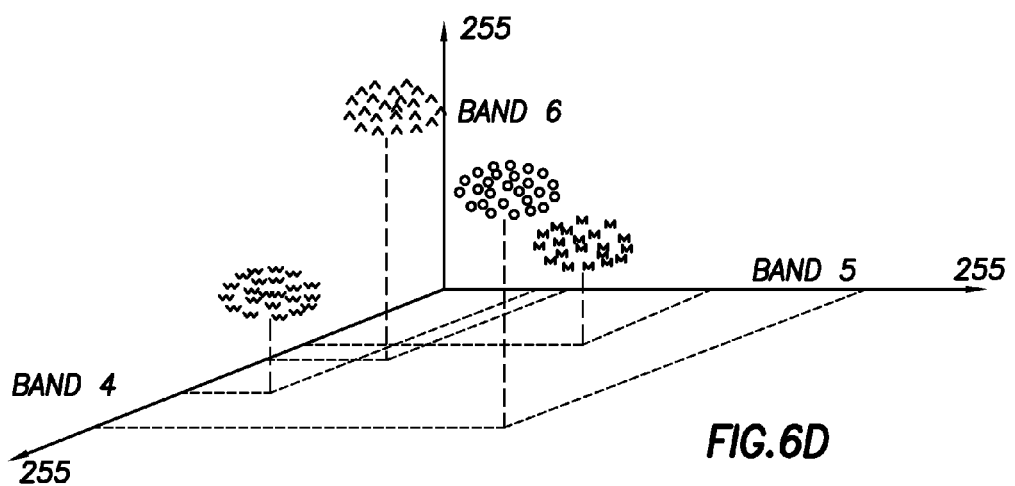

In one or more embodiments of the invention, the historical data may include statistics of images (e.g., mean and standard deviation of pixel intensity in a histogram of the images) obtained from monitoring the reflected atmospheric radiation and the surface emission without the presence of hydrocarbons. In one or more embodiments of the invention, the image stream obtained during calibration is classified based on a parametric classification method, i.e., by comparing the associated statistics to generate the historical data. In one or more embodiments of the invention, historical data may further include objects identified from the statistics based on rule based classification. For example, statistics derived from known images (e.g., a portion of the platform, a moving kelp bed, etc.) within the monitoring area during the calibration phase may be identified as a known object based on a heuristic rule. Furthermore, statistics derived from known images of oil film with known thickness and composition may also be identified as a known object to be included in the historical data based on the heuristic rule. For example, FIGS. 5A-5C may be identified as light oil covered water surface, native water surface, and heavy oil covered water surface, respectively. In one or more embodiments of the invention, the collection of known objects in historical data may be supplemented with characterization analysis data each time hydrocarbon is detected during the monitoring phase.

In Step 708, an image stream is obtained from monitoring the reflected atmospheric radiation and the surface emission, for example using any of the sensors C1-C4. A statistical diagram (e.g., a histogram) may then be generated from the image stream (Step 710). In one or more embodiments of the invention, multiple image streams may be obtained from multiple sensors to generate a multi-dimensional statistical diagram (e.g., any one of the multi-dimensional histograms depicted in FIG. 6A-6D) (Step 710). In one or more embodiments of the invention, the multiple image streams may be obtained in any of multiple visible bands, multiple NIR bands, multiple LWIR bands, fluorescent bands, and/or a Raman effect.

In Step 712, clusters (e.g., clusters of dots depicted in FIG. 6A-6D) are identified in the statistical diagram. In one or more embodiments of the invention, the statistical diagram is pre-processed (e.g., using the workflow of FIGS. 3A-3B) prior to identifying the clusters.

In Step 714, the presence of hydrocarbons is detected based on the clusters according to the decision tree described above. In one or more embodiments of the invention, the presence of hydrocarbons is detected by comparing the clusters to historical data generated during a calibration phase. In one or more embodiments of the invention, the hydrocarbon detection is validated by comparing the clusters to historical data (Step 716). In one or more embodiments of the invention, the comparison is performed by comparing statistics (e.g., means and standard deviation of a histogram) of the clusters and historical data in a parametric classification method. In one or more embodiments of the invention, the comparison is performed by comparing the clusters to objects (e.g., corresponding to known images such as portions of the platform, moving kelp bed, oil film with known thickness and composition, etc.) in the historical data using a rule based classification method.

In one or more embodiments of the invention, the surface may be irradiated using ultraviolet source, visible light source, and/or infrared source to improve the radiance contrast. In one or more embodiments of the invention, the surface may be irradiated using ultraviolet source and/or visible light source to generate fluorescence response. In one or more embodiments of the invention, the surface may be irradiated using ultraviolet source and/or visible light source to generate Raman signal.

In one or more embodiments of the invention, an area associated with the presence of the hydrocarbon on the surface is calculated and tracked for generating an alert based on the area exceeding a pre-determined threshold.

Figure 8A:
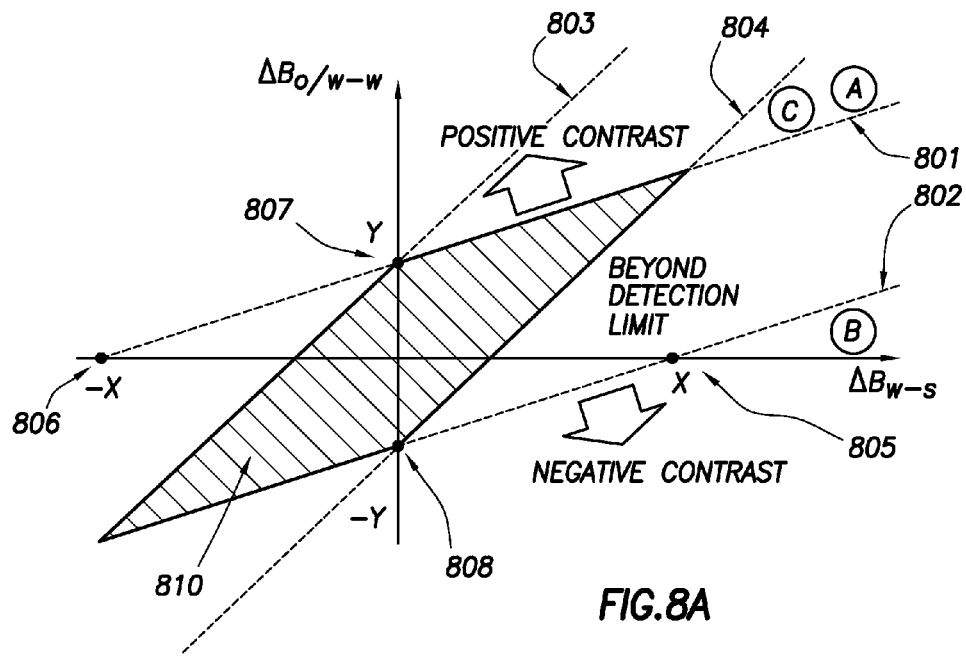
FIGS. 8A-8B show an exemplary diagram of portions of an emissivity contrast model for oil detection in accordance with one or more embodiments of the invention.
Figure 8B:
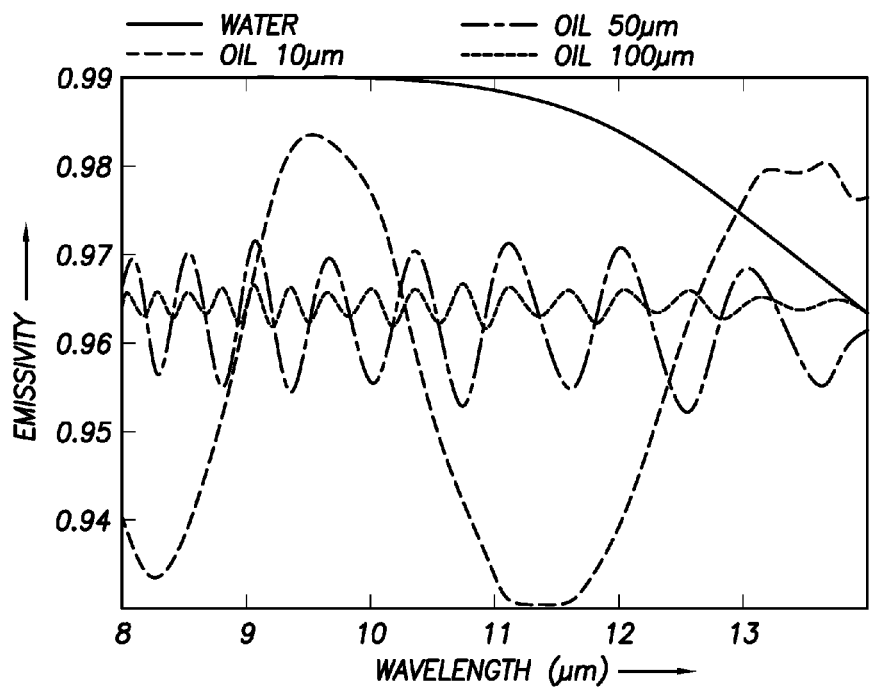

As described above, the radiance contrast model may include capabilities for modeling reflection contrast, temperature contrast, emissivity contrast, or suitable contrast based on other physical mechanisms. FIGS. 8A-8B show exemplary diagrams of portions of an emissivity contrast model for oil detection in accordance with one or more embodiments of the invention.

In LWIR remote sensing, total radiance collected by a detector (or sensor) has four possible components: (a) emission from materials (e.g., air or smoke between the monitored surface and the detector within the line of sight of the detector, (b) surface emission (e.g., thermal emission), (c) direct solar illumination, and (d) reflected sky radiance. Terms (a) and (c) can be neglected for short-range applications without directing the detector toward the sun. Thus, the radiance difference ($\Delta L$) due to thermal emission (i.e., temperature contrast) between oil covered surface and native water surfaces can be described using Equation 4 below.

$$\Delta L = \Delta\epsilon_{oil/water-water}\Delta B_{water-sky} + \epsilon_{oil/water}\Delta B_{oil/water-water} \quad \text{Equation 4}$$

$\Delta\epsilon_{oil/water-water}$ is the emissivity difference between the oil covered surface and the native water surface. $\Delta B_{water-sky}$ is the black body radiation difference between the native water surface and the sky. $\epsilon_{oil/water}$ is the emissivity of the oil covered water surface. $\Delta B_{oil/water-water}$ is the black body radiation difference between the oil covered water surface and the native water surface. Note that Equation 4 is applicable to monochromatic radiation as well as polychromatic radiation as long as proper integration over a wavelength band is carried out.

Using the differences in black body radiation (i.e., $\Delta B_{water-sky}$ and $\Delta B_{oil/water-water}$) as independent variables, exemplary detection boundaries due to detector sensitivity are delineated in FIG. 8A by two lines (801) and (802). As described above, $B_{water-sky}$ and $\Delta B_{oil/water-water}$ relates to radiometric temperatures of oil, water, and sky. The intercepts of lines (801) and (802) with respect to the horizontal and vertical axes are $(X,Y)=(\delta T/\Delta\epsilon_{oil/water-water}, \delta T/\epsilon_{oil/water})$ where $\delta T$ is the sensitivity of the detector represented in black body radiation equivalent unit.

In most practical conditions, both $\Delta B_{water-sky}$ and $\Delta B_{oil/water-water}$ are positive, therefore the upper right quadrant of FIG. 8A is of particular interest. As shown in FIG. 8A. positive contrast (i.e., where oil covered water surface is brighter than the native water surface) is observed in the region (e.g., (A)) above the upper detection boundary (801), negative contrast (i.e., where oil covered water surface is darker than the native water surface) is observed in the region (e.g., (B)) below the lower detection boundary (802), and the region in between (801) and (802) represents a range of radiance contrast outside the sensitivity (or detectable) range of the detector. Note that for current commercial microbolometers with thermal sensitivity ~80 mK, the intercepts are $(X,Y)\sim(300,6.2)$ ($\mu Wcm^{-2}$ $str^{-1}$) for a typical crude oil. In addition, since $X \gg Y$ for this case, the detection boundary intercept X is much further out on the X axis than shown in FIG. 8A, where the scale is exaggerated for illustration.

In one or more embodiments of the invention, the thickness dependent emissivity model is described by Equations 5-7 below. Starting from radiative transfer theory, total emitted energy of oil covered water surface (e.g. (120) over (121) as depicted in FIG. 1) can be considered as the sum of two contributions: the energy (106) emitted by the water, as seen through the film (120), and the energy (105) emitted by the film (120). For the oil film contribution, the emission can be obtained by integrating the intensity of the electromagnetic waves emitted from individual volumetric elements at position y in the film over the entire film thickness h to generate the Equation 5 below.

$$I_{oil} = \frac{\lambda}{4\pi k_2}\left|\frac{t_{12}}{1-r_{21}r_{23}e^{i(2\pi/\lambda)\hat{n}_2(h/\cos\theta_2)}}\right|^2 (1-e^{-4\pi k_2 h/\lambda}) \quad \text{Equation 5}$$

where r and t are the interfacial amplitude reflectivity and transmissivity, respectively. Subscripts ij denotes the direction of wave propagation from medium i to j where 1 represents air, 2 represents oil, and 3 represents water. $\hat{n}_t$ is the complex refractive index of medium i. $\theta_2$ is the angle of refraction in the film. By definition, the emissivity contributed by the film is obtained by the ratio of the Poynting vectors of the emitted intensity to the original intensity as shown in Equation 6 below.

$$\varepsilon_{oil} = Re\left\{\frac{\hat{n}_1}{\hat{n}_2}\right\}\frac{4\pi k_2}{\lambda}I_{oil} \qquad \text{Equation 6}$$

Similarly, the emission from the water and the equivalent partial emissivity can be calculated as shown in Equation 7 below.

$$I_{water} = \frac{\lambda}{4\pi k_3}\left|\frac{t_{21}t_{32}}{1-r_{21}r_{23}e^{i(2\pi/\lambda)\hat{n}_2(h/\cos\theta_2)}}\right|^2 e^{-4\pi k_2 h/\lambda} \qquad \text{Equation 7}$$

$$\varepsilon_{water} = Re\left\{\frac{\hat{n}_1}{\hat{n}_3}\right\}\frac{4\pi k_3}{\lambda}I_{water}$$

The total emissivity can then be calculated by summing the individual contributions from the oil and the water. It can be seen that as the film thickness approaches zero, the emissivity is contributed entirely by the underlying water, while on the other extreme all by the oil film.

FIG. 8B shows the emissivity of the oil covered water surface and native water surface for three different oil film thicknesses. It is observed that the frequency of the sinusoidal emissivity fluctuation increases as the oil film thickness increases. In one or more embodiments of the invention, the thickness dependent emissivity may be used in conjunction with the detection boundaries delineated in FIG. 8A to detect contrast variations (i.e., change in temperature contrast) in different sub-bands (i.e., sub-wavelength channels) in a wavelength band. For example, with multiple bandpass filters to assure decent sampling across the LWIR band, sinusoidal contrast variations (called spectral contrast as the variations are observed at different sub-wavelength) can be detected from the oil covered surface, whereas flat response (8-10.5 μm) and monotonically decreasing trend (>10.5 μm) is observed (therefore no spectral contrast observed) from a native water surface. In FIG. 8A, the detection boundaries (801) and (802) may correspond to the 9.5 μm sub-wavelength channel in the LWIR band, which are rotated counterclockwise to the detection boundaries (803) and (804) for the 8.5 μm sub-wavelength channel, reflecting changes in $\Delta\varepsilon_{oil/water-water}$ and $\varepsilon_{oil/water}$ shown in FIG. 8B. Accordingly, the undetectable range of environmental conditions in which temperature contrast falls outside the sensitivity range of the detector may be reduced from the entire region between (801) and (802) to the nominally diamond shaped region (810) by using multiple sub-wavelength channels (e.g., both 9.5 μm and 8.5 μm). At the same time, contrast variations (i.e., spectral contrast resulted from change in temperature contrast) results from the use of different sub-wavelength channels without change in radiometric temperature differences (i.e., both $\Delta B_{water-sky}$ and $\Delta B_{oil-water}$ are fixed). For example, considering a particular environmental condition corresponding to point (C) in FIG. 8B, positive contrast is observed using 9.5 μm sub-wavelength channel while negative contrasts is observed using 8.5 μm sub-wavelength channel whereas, for a native water surface without oil film, the signals from these two sub-wavelength channels will be similar without such variation (i.e., no spectral contrast). This multi-sub-wavelength-channel scheme provides a novel detection mechanism based entirely on wavelength dependent contrast induced by thin oil films. As noted above, FIG. 8A is for illustrative purposes and not drawn to scale. Although not shown in FIG. 8A, the X,Y intercepts of (803) and (804) may deviate from that of (801) and (802).

Furthermore, since the oil film is unlikely to be spatially uniform in thickness, a detection mechanism similar to detecting the spectral contrast may be devised to detect spatial variations in the oil film thickness. As shown in FIG. 8B, the DC level (i.e., the baseline) of the sinusoidal emissivity increases as the oil film becomes thicker. In one or more embodiments of the invention, such detection mechanism may be employed to detect thickness contrast by mapping out the radiance variation resulted from spatial thickness distribution of the oil film.

It is important to note that the spectral and thickness contrasts are effective detection mechanisms under all environmental conditions, for example day/night, warm/cold sky, and with/without differential heating. In one or more embodiments of the invention, the radiance contrast model models the spectral contrast and the thickness contrast for environmental conditions, including daytime, nighttime, warm sky, cold sky, with differential heating, and without differential heating.

Figure 9:
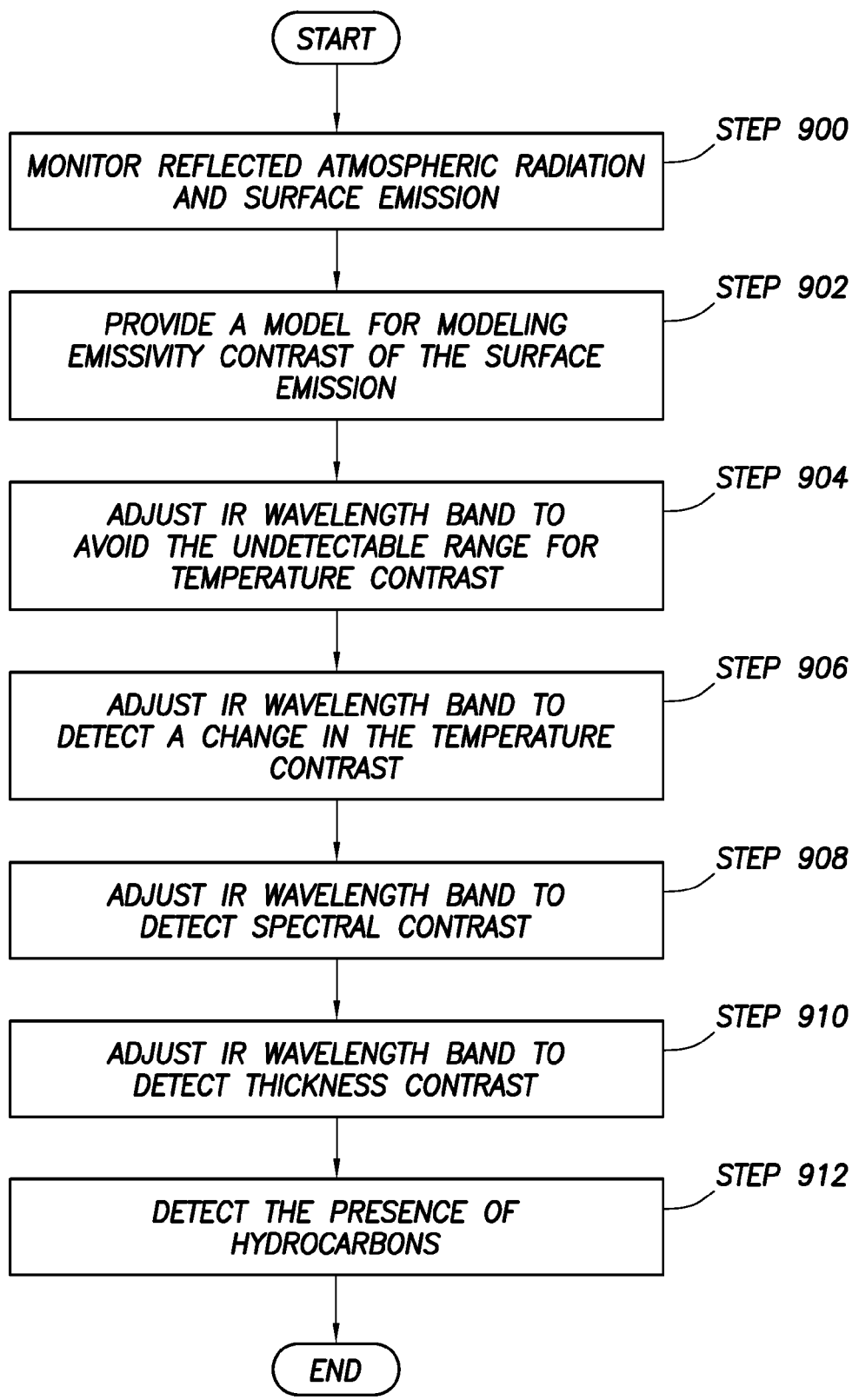
FIG. 9 shows a flow chart of a method based on the model of FIGS. 8A-8B in accordance with one or more embodiments of the invention.

FIG. 9 is a flow chart of a method based on the model of FIGS. 8A-8B. The process shown in FIG. 9 may be used, for example, by the oil detection system of FIG. 2. Those skilled in the art, having the benefit of this detailed description, will appreciate the sequence of steps shown in FIG. 9 may differ among embodiments of the invention, and that one or more of the steps may be optional. In one or more embodiments of the invention, one or more of the steps shown in FIG. 9 may be omitted, repeated, and/or performed in a different order than that shown in FIG. 9. Accordingly, the specific arrangement of steps shown in FIG. 9 should not be construed as limiting the scope of the invention.

Initially, surface emission (e.g., thermal emission) from a surface (e.g., water surface) is monitored in an infrared band (e.g., LWIR band) (Step 900).

In Step 902, a model is provided for modeling emissivity contrast of the surface emission. For example, the emissivity contrast may be induced by the presence of hydrocarbons on the water surface. In one or more embodiments of the invention, the model may be as described with respect to FIGS. 8A-8B. In one or more embodiments of the invention, the model is capable of modeling temperature contrast, spectral contrast, and thickness contrast. In one or more embodiments of the invention, the model comprises an undetectable range (e.g., as depicted in FIG. 8A) for the temperature contrast based on radiometric temperatures of oil, water, and sky (e.g., as described by Equations 4-7). In one or more embodiments of the invention, the undetectable range is modeled as dependent on a wavelength of the infrared band (e.g., a sub-wavelength channel).

In Step 904, the wavelength of the infrared band is adjusted to avoid the undetectable range to detect the hydrocarbon based on the temperature contrast. In one or more embodiments of the invention, the undetectable range is rotated in $\Delta B_{water-sky}/\Delta B_{oil/water-water}$ plane by adjusting the sub-wavelength channel according to the particular environmental condition (e.g., as depicted in FIG. 8A).

In one or more embodiments of the invention, the model comprises a positive range and a negative range for the temperature contrast (e.g., as depicted in FIG. 8A) based on radiometric temperatures of oil, water, and sky (e.g., as described by Equations 4-7). In one or more embodiments of the invention, the positive range and the negative range is modeled as dependent on a wavelength of the infrared band (e.g., a sub-wavelength channel). In one or more embodiments of the invention, the wavelength of the infrared band is adjusted to detect a change in the temperature contrast for detecting the presence of hydrocarbons (Step 906).

In one or more embodiments of the invention, the model comprises a wavelength dependent emissivity model (e.g., as depicted in FIG. 8B) for the spectral contrast. In one or more embodiments of the invention, a wavelength of the infrared band (e.g., a sub-wavelength channel) is adjusted to detect the spectral contrast for detecting the presence of hydrocarbons (Step 908).

In one or more embodiments of the invention, the model comprises a thickness dependent emissivity model (e.g., as depicted in FIG. 8B) for the thickness contrast induced by a thickness variation of hydrocarbon. In one or more embodiments of the invention, a wavelength of the infrared band (e.g., a sub-wavelength channel) is adjusted to detect the thickness contrast for detecting the presence of hydrocarbons (Step 910).

In Step 912, the presence of hydrocarbon is detected from the surface emission based on the emissivity contrast model, for example by detecting the temperature contrast, the change in the temperature contrast, the spectral contrast, and/or the thickness contrast of the oil covered water surface with respect to the native water surface in a monitored area.

The invention has numerous advantages, such as, but not limited to those listed below. In one or more embodiments of the invention, the current invention provides an inexpensive, permanent monitoring sensory system by using thermal imaging capability that can be widely deployed over a wide geographic area. In one or more embodiments of the invention, the current invention overcomes other technical obstacles to deploying such systems in an offshore environment, including the lack of network infrastructure to convey the data from an unmanned platform to a manned platform and the lack of electrical power on most unmanned platforms.

It will be understood from the foregoing description that various modifications and changes may be made in the preferred and alternative embodiments of the present invention without departing from its true spirit. For example, sensors, image processing steps, decision tree workflow, radiance contrast model, and arrangement of the system may be selected or adjusted to achieve the desired detection. The method steps may be repeated according to the various configurations for different environmental conditions, and the results compared and/or analyzed. Although examples are given to describe oil spill detection, this detection technology may also be applied in hydrocarbon exploration, production, and refining.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A method for detecting presence of hydrocarbons on a surface, comprising:
monitoring reflected atmospheric radiation corresponding to a first intensity and surface emission from the surface corresponding to a second intensity to generate an image comprising a plurality of pixels, wherein each of the plurality of pixels is associated with the first intensity obtained using a first sensor corresponding to a first spectral band and the second intensity obtained using a second sensor corresponding to a second spectral band, wherein the first sensor and the second sensor have overlapping field of views, wherein the first intensity and the second intensity are obtained simultaneously;
detecting the presence of the hydrocarbons based on the reflected atmospheric radiation and the surface emission by:
generating a multi-dimensional histogram in a multi-dimensional space having a first dimension corresponding to the first intensity and a second dimension corresponding to the second intensity; and
identifying one or more clusters in the multi-dimensional histogram, wherein the one or more clusters correspond to the presence of the hydrocarbons; and
generating an alert based on the presence of the hydrocarbons.

2. The method of claim 1 wherein said monitoring is accomplished using at least one selected from a group consisting of a visible camera, a near-infrared camera, and a long-wavelength-infrared (LWIR) camera.

3. The method of claim 1, wherein the surface is a water surface.

4. The method of claim 1, further comprising:
calculating a statistical parameter indicating a possible extent of the presence of the hydrocarbon on the surface, wherein the alert is generated based on the statistical parameter being outside of a pre-determined range.

5. The method of claim 1, further comprising:
providing a model for modeling radiance contrast of the reflected atmospheric radiation and the surface emission in at least one selected from a group consisting of daytime condition, nighttime condition, and pre-determined weather condition, wherein the radiance contrast is induced by the presence of the hydrocarbons on the surface and comprises at least one selected from a group consisting of reflection contrast, temperature contrast, and emissivity contrast; and
defining a decision tree based on the model,
wherein the presence of the hydrocarbons is detected according to the decision tree.

6. The method of claim 5,
wherein the presence of the hydrocarbons is detected based on the one or more clusters according to the decision tree.

7. The method of claim 6, wherein the multi-dimensional histogram comprises a mean intensity and a standard deviation.

8. The method of claim 6,
wherein at least one selected from a group consisting of the first spectral band and the second spectral band comprises at least one selected from a group consisting of a first visible band, a second visible band, a first near-infrared (NIR) band, a second NIR band, a first long-wavelength-infrared (LWIR) band, a second LWIR band, a fluorescent band, and a Raman effect.

9. The method of claim 8, wherein the first intensity and the second intensity are obtained using a bandpass filter.

10. The method of claim 8, further comprising:
calibrating the model without the presence of the hydrocarbons to generate historical data, wherein the decision tree comprises a comparison based on the historical data; and
comparing the one or more clusters to historical data according to the decision tree to validate the detection of the presence of the hydrocarbons.

11. The method of claim 10,
wherein historical data comprises statistics of a plurality of images obtained from monitoring the reflected atmospheric radiation and the surface emission without the presence of the hydrocarbons,
wherein the statistics are generated based on parametric classification,
wherein historical data further comprises one or more objects identified from the statistics based on rule based classification, and
wherein the one or more clusters are compared to the one or more objects in the historical data to validate the detection of the presence of the hydrocarbons.

12. The method of claim 5, further comprising:
irradiating the surface using at least one selected from a group consisting of ultraviolet source, visible light source, and infrared source to improve the radiance contrast.

13. The method of claim 5, further comprising:
irradiating the surface using at least one selected from a group consisting of ultraviolet source and visible light source to generate fluorescence response.

14. The method of claim 5, further comprising:
irradiating the surface using at least one selected from a group consisting of ultraviolet source and visible light source to generate Raman signal.

15. A system for detecting presence of hydrocarbons on a surface, comprising:
a first sensor and a second sensor for monitoring reflected atmospheric radiation corresponding to a first intensity and surface emission from the surface corresponding to a second intensity to generate an image comprising a plurality of pixels, wherein each of the plurality of pixels is associated with the first intensity obtained using the first sensor corresponding to a first spectral band and the second intensity obtained using the second sensor corresponding to a second spectral band, wherein the first sensor and the second sensor have overlapping field of views, wherein the first intensity and the second intensity are obtained simultaneously; and
a memory and a processor, embodying instructions stored in the memory and executable by the processor, the instructions comprising functionality to detect the presence of the hydrocarbons based on the reflected atmospheric radiation and the surface emission according to a decision tree by:
generating a multi-dimensional histogram in a multi-dimensional space having a first dimension corresponding to the first intensity and a second dimension corresponding to the second intensity;
identifying one or more clusters in the multi-dimensional histogram, wherein the one or more clusters correspond to the presence of the hydrocarbons,
wherein the decision tree is based on a model for modeling radiance contrast of the reflected atmospheric radiation and the surface emission in at least one selected from a group consisting of daytime condition, nighttime condition, and pre-determined weather condition,
wherein the radiance contrast is induced by the presence of the hydrocarbons on the surface and comprises at least one selected from a group consisting of reflection contrast, temperature contrast, and emissivity contrast; and
generating an alert based on the presence of the hydrocarbons.

16. The system of claim 15, wherein said monitoring is accomplished using at least one selected from a group consisting of a visible camera, a near-infrared camera, and a long-wavelength-infrared (LWIR) camera.

17. The system of claim 15, wherein the surface is a water surface.

18. The system of claim 15, the instructions further comprising functionality to:
calculate a statistical parameter indicating a possible extent of the presence of the hydrocarbon on the surface,
wherein the alert is generated based on the statistical parameter being outside of a pre-determined range.

19. The system of claim 15,
wherein the presence of the hydrocarbons is detected based on the one or more clusters according to the decision tree.

20. The system of claim 19, wherein the statistical diagram comprises a histogram of pixel intensity, wherein the histogram comprises a mean intensity and a standard deviation.

21. The system of claim 19, the instructions further comprising functionality to:
obtain a second image stream from monitoring the reflected atmospheric radiation and surface emission; and
further generate the statistical diagram from the second image stream,
wherein the statistical diagram is a multi-dimensional statistical diagram, and
wherein at least one selected from a group consisting of the first image stream and the second image stream are obtained from at least one selected from a group consisting of a first visible band, a second visible band, a first near-infrared (NIR) band, a second NIR band, a first long-wavelength-infrared (LWIR) band, a second LWIR band, a fluorescent band, and a Raman effect.

22. The system of claim 19, the instructions further comprising functionality to:
calibrate the model without the presence of hydrocarbons to generate historical data, wherein the decision tree comprises a comparison based on the historical data; and
compare the one or more clusters to historical data according to the decision tree to validate the detection of the presence of hydrocarbons.

23. The system of claim 22,
wherein historical data comprises statistics of a plurality of images obtained from monitoring the reflected atmospheric radiation and the surface emission without the presence of hydrocarbons,
wherein the statistics are generated based on parametric classification,
wherein historical data further comprises one or more objects identified from the statistics based on rule based classification, and
wherein the one or more clusters are compared to the one or more objects in the historical data to validate the detection of the presence of hydrocarbons.

* * * * *